United States Patent [19]

Edens et al.

[11] Patent Number: 4,657,857

[45] Date of Patent: Apr. 14, 1987

[54] YEAST OF THE GENUS KLUYVEROMYCES MODIFIED FOR THE EXPRESSION OF PREPROTHAUMATIN OR ITS VARIOUS ALLELIC AND MODIFIED FORMS OR THEIR MATURATION FORMS, AND THE PROTEINS OBTAINED BY THAT EXPRESSION

[75] Inventors: Luppo Edens, Maassluis; Adrianus Ledeboer, Rotterdam; Cornelis Verrips, Maassluis; Johannes A. Van den Berg, Reeuwijk, all of Netherlands

[73] Assignee: Internationale Octrooi Maatschappij "Octropa" B.V., Rotterdam, Netherlands

[21] Appl. No.: 570,984

[22] PCT Filed: May 19, 1983

[86] PCT No.: PCT/EP83/00129

§ 371 Date: Jan. 18, 1984

§ 102(e) Date: Jan. 18, 1984

[87] PCT Pub. No.: WO83/04051

PCT Pub. Date: Nov. 24, 1983

[30] Foreign Application Priority Data

May 19, 1982 [NL] Netherlands .................... 8202091

[51] Int. Cl.$^4$ .................... C12P 21/00; C12N 15/00; C12N 1/00

[52] U.S. Cl. .................... 435/68; 435/172.3; 435/317; 435/255; 935/28; 935/56; 935/69; 935/11

[58] Field of Search .................... 435/172.3, 68, 317, 435/255; 935/9, 10, 11, 28, 22, 41, 69

[56] References Cited

FOREIGN PATENT DOCUMENTS 0054330 6/1982 European Pat. Off. ......... 435/172.2
0054331 6/1982 European Pat. Off. ......... 435/172.2

OTHER PUBLICATIONS

Edens et al, 1982, "Cloning of CDNA Encoding the Sweet-Tasting Plant Thaumatin and its Expression in *E. coli*", *Gene*, v 18, pp. 1–12.

Struhl et al, 1979, "High-Frequency Transformation of Yeast: Autonomous Replication of Hybrid DNA Molecules", *Proc Natl Acad Sci*, v 76, 1035–1039.

Edens et al, 1984, "Synthesis and Processing of the Plant Protein Thaumatin in Yeast", *Cell*, v 37, pp. 629–633.

Holland et al, 1980, "Structural Comparison of Two Nontandemly Repeated Yeast Glyceraldehyde-3-Phosphate Dehydrogenase Genes", *J. Biol. Chem*, v 255, 2596–2605.

Cover of *Gene*, v 18 No. 1, Apr. 1982.

*Primary Examiner*—Thomas G. Wiseman
*Assistant Examiner*—Joanne M. Giesser
*Attorney, Agent, or Firm*—Cushman, Darby & Cushman

[57] ABSTRACT

The invention relates to yeasts of the genus Kluyveromyces, in particular *K. lactis*, acting as hosts for the expression of preprothaumatin or its various allelic and modified forms or their maturation forms, which yeasts contain an rDNA plasmid comprising a structural gene encoding for a thaumatin-like protein, an autonomous replicating sequence derived from *K. lactis* (KARS), a yeast regulon derived from the GAPDH-genes of *S. cerevisiae*, and a selection marker, e.g. the trp-1 or the lac-4 gene from *S. cerevisiae* and *K. lactis*, respectively. Optionally the plasmid also contains a transcription terminator from a yeast. Further the preparation of such yeasts and the preparation of thaumatin-like proteins with such yeasts and the proteins so obtained are claimed. The yeast described give a better expression than obtained with *E. coli* as described in EP-PA (A2) 0 054 330 and 0 054 331, published on June 23, 1982.

9 Claims, 11 Drawing Figures

FIG. 1

FIG. 7

```
      -840       -830       -820       -810       -800       -790
GAATTCCTCA GTTTCAAGAT CTTTTAATGT CCAAAACCAT TTGAGCCGAT CTAAATACTT
      -780       -770       -760       -750       -740       -730
CTGTGTTTTC ATTAATTTAT AAATTGTACT CTTTTAAGAC ATGGAAAGTA CCAACATCCG
      -720       -710       -700       -690       -680       -670
TTGAAACAGT TTTTCATTTA CATATGGTTT ATTGGTTTTT CCAGTGAATG ATTATTTGTC
      -660       -650       -640       -630       -620       -610
GTTACCCTTT CGTAAAACTT CAAACACGTT TTTAAGTATT GTTAGTTGC TCTTTCGACA
      -600       -590       -580       -570       -560       -550
TATATGATTA TCCCTGCGCG GCTAAAGTTA AAGATGCAAA AAACAGAAGA CAACTGAAGT
      -540       -530       -520       -510       -500       -490
TAATTTACGT CAATTAAGTT TTCCAGGGTA ATGATGTTTT GGGCTTCCAC TAATTCAATA
      -480       -470       -460       -450       -440       -430
AGTATGTCAT GAAATACGTT GTGAAGAGCA TCCAGAAATA ATGAAAAGAA ACAACGAAAC
      -420       -410       -400       -390       -380       -370
TGGGTCGGCC TGTTGTTTCT TTTCTTTACC ACGTGATCTG CGGCATTTAC AGGAAGTCGC
      -360       -350       -340       -330       -320       -310
GCGTTTTGCG CAGTTGTTGC AACGCAGCTA CGGCTAACAA AGCCTAGTGG AACTCGACTG
      -300       -290       -280       -270       -260       -250
ATGTGTTAGG GCCTAAAACT GGTGGTGACA GCTGAAGTGA ACTATTCAAT CCAATCATGT
      -240       -230       -220       -210       -200       -190
CATGGCTGTC ACAAAGACCT TGCGGACCGC ACGTACGAAC ACATACGTAT GCTAATATGT
      -180       -170       -160       -150       -140       -130
GTTTTGATAG TACCCAGTGA TCGCAGACCT GCAATTTTTT TGTAGGTTTG GAAGAATATA
      -120       -110       -100        -90        -80         -70
TAAAGGTTGC ACTCATTCAA GATAGTTTTT TTCTTGTGTG TCTATTCATT TTATTATTGT
       -60        -50        -40        -30        -20         -10
TTGTTTAAAT GTTAAAAAAA CCAAGAACTT AGTTTCAAAT TAAATTCATC ACACAAACAA
        -1
ACAAAACAAA ATG
```

FIG. 2

```
         7         17         27         37         47         57
TAAATTTAAC TCCTTAAGGT TACTTTAATG ATTTAGTTTT TATTATTAAT AATTCATGCT
        67         77         87         97        107        117
CATGACATCT CATATACACG TTTATAAAAC TTAAATAGAT TGAAAATGTA TTAAAGATTC
       127        137        147        157        167        177
CTCAGGGATT CGATTTTTTT GGAAGTTTTT GTTTTTTTTT CCTTGACATG CTGTAGTATT
       187        197        207        217        227        237
TGGGAACAAT TATACAATCG AAAGATATAT GCTTACATTC GACCGTTTTA GCCGTGATCA
       247        257        267        277        287        297
TTATCCTATA GTAACATAAC CTGAAGTATA ACTGACACTA CTATCATCAA TACTTGTCAC
       307        317        327        337        347        357
ATGAGAACTC TGTGAATAAT TAGGCCACTG AAATTTGATG CCTGAAGGAC CGGCATCACG
       367        377        387        397        407        417
TATCTTCGAT AAAGCACTTA GTATCACACT AATTGGCTTT TCGCCGCATA TGGTGTTTCC
       427        437        447        457        467        477
GGTGATTTCC AAGTATTGTT TCCAAGCATC GTACCTTTCA CCATTTGGAG TATCACTTAG
       487        497        507        517        527        537
CGTTTTCATC GCATATCTGT CCATTATTTC AATGGATTGC CAAATGGGAA CTTGATGATG
       547        557        567        577        587        597
TGAAAGTTTA CTCCTAGCAG TTAACATTTC CACTTCTGTT TCCTCTTTAA TGGCATTCAT
       607        617        627        637        647        657
TCAACTCTTC CTTGCTTACC GACGTACCCG TATATTGGAA TCTGCGGCCC CAATGACAGA
       667        677        687        697        707        710
AATCACTGCT TACAATGAAT AAATTGTTCG GATCCTTAAT GTACTCCGAC AAAATATTAC
       727        737        747        757        767        777
CAATGCAACG ATCAACATCA ACGCTGTTAT GAGAAACCAT CATGGAATT ACCTTCACCG
       787        797        807        817        827        837
TATCTAAAGA AATTTCTCTC CATTTCAAAG TTTCCACCAA CATGGGGAGC TGCATCTCTA
       847        857        867        877        887        897
AGGAATGTTC AGCCATATCA GTGTCATGAT CCATTGGCTT AAACAGCTTC TTTCCGTTCT
       907        917        927        937        947        957
CAGGATACTC CTTCTGTATT AATGTTTTAC ACAAGTCTGT ATCCACTTTC AGATTACCCA
       967        977        987        997       1007       1017
AGGGCGTCTC TAGCTCACTG AATGCACTAA CTAAAATTTG GTTTTTGAAA TAGATGTGAT
      1027       1037       1047       1057       1067       1077
GCGACGGCCC CAAGATAAAT ATTCTCTTAA CATTACGGTT CAAATCCAAC GATGCGTACG
      1087       1097       1107       1117       1127       1137
AGTAGGCCAT AGTGGGTCCA CAATACCTGT AACCGGCATG AGGACATATG ATAATTCTGG
      1147       1157       1167       1177       1187       1197
CGTTGTGAAT TGGGCCTTTA AGGGTACTTT TGATCAAGTA TGTATGCGGT TGTTGAGATA
      1207       1217       1227       1237       1247       1257
ATTCTTGGGC TCTATTGGAA TACCATGAGC CTGCATGTGT TGCTGGACGT ATTGACATGT
      1267       1277       1287       1297       1307       1317
TTGAAAAATT CTATTCTTTG CACTGTAGTC CACCTAAGCC ACCGACTAGG ACCACTTCAC
      1322
TTAAG
```

F I G. 3

FIG. 4

```
                           Sac I
5' CCC.TTA.GTT.TCA.AAT.TAA.AGA.GCT.CAT.CAC 3'
           3' TCT.CGA.GTA.GTG.TCT.TTG.TTT.GTT.TTG.TTT 5'

Klenow DNA-polymerase
                       dNTP's

Dde I              Sac I
5' CCC.TTA.GTT.TCA.AAT.TAA.AGA.GCT.CAT.CAC.ACA.AAC.AAA.CAA.AAC.AAA 3'
3' GGG.AAT.CAA.AGT.TTA.ATT.TCT.CGA.GTA.GTG.TCT.TTG.TTT.GTT.TTG.TTT 5'

Dde I
               Sac I
5' TTA.GTT.TCA.AAT.TAA.AGA.GCT.CAT.CAC.ACA.AAC.AAA.CAA.AAC.AAA 3'
    3' CAA.AGT.TTA.ATT.TCT.CGA.GTA.GTG.TCT.TTG.TTT.GTT.TTG.TTT 5'

Sac I

T₄ DNA-polymerase, dNTP's
           T₄ DNA ligase

5' TTA.GTT.TCA.AAT.TAA.AGC.ATC.ACA.CAA.ACA.AAC.AAA.ACA.AA 3'
3' CAA.AGT.TTA.ATT.TCG.TAG.TGT.GTT.TGT.TTG.TTT.TGT.TT 5'
```

YEAST OF THE GENUS KLUYVEROMYCES MODIFIED FOR THE EXPRESSION OF PREPROTHAUMATIN OR ITS VARIOUS ALLELIC AND MODIFIED FORMS OR THEIR MATURATION FORMS, AND THE PROTEINS OBTAINED BY THAT EXPRESSION

The present invention relates to the microbiological preparation of preprothaumatin and related compounds, which preparation has been made possible by recombinant DNA techniques. In European patent applications (A2) 0 054 330 and 0 054 331, both published on June 23, 1982, DNA sequences encoding various allelic forms of preprothaumatin, their maturation forms such as prethaumatin, prothaumatin and thaumatin, and modified forms thereof, as well as cloning vehicles comprising said DNA sequences, their use in transforming micro-organisms, in particular *E. coli,* and the preparation of thaumatin like proteins are described.

For the production to be commercially attractive, the yields obtained with *E. coli* are not high enough, so that a need exists for microbiological systems which are capable of producing the thaumatin-like proteins in far higher amounts. By thaumatin-like proteins are meant preprothaumatin, its various allelic or modified forms, and their maturation forms such as prethaumatin, prothaumatin and thaumatin.

It has now been found that the structural genes described in the above-mentioned European patent applications can be combined with autonomously replicating sequences originating from *Kluyveromyces lactis* (so-called KARS), with a selection marker and with a yeast regulon into a plasmid, which plasmid can be brought into yeast cells of the Kluyveromyces genus, which then become capable of producing the thaumatin-like proteins. In this way expression of the thaumatin-like proteins in yeast cells succeeded.

Therefore, the present invention provides a yeast of the genus Kluyveromyces containing a recombinant DNA plasmid comprising:

(i) a structural gene encoding for preprothaumatin or its various allelic or modified forms or their maturation forms, (ii) an autonomously replicating sequence originating from *Kluyveromyces lactis* (so-called KARS), (iii) a yeast regulon derived from the glyceraldehyde-3-phosphate dehydrogenase (GAPDH) genes of *Saccharomyces cerevisiae,* and (iv) a selection marker, such as the trp-1 or the lac-4 gene.

In this way a much improved expression of the desired proteins could be obtained, so that commercial application comes more within reach.

Preferably the plasmid also contains a transcription terminator derived from a yeast, and/or a centromer and/or a replicating region derived from a yeast.

Good results have been obtained with a *Kluyveromyces lactis* yeast, but it is very probable that other Kluyveromyces species will be effective as well. The structural genes are preferably selected from the group consisting of the structural genes disclosed in the above-mentioned European patent applications.

Successful KARS-sequences were isolated from the wild strain *K. lactis* CBS 2360, as will be described below.

For transformation purposes in *K. lactis* it is desirable to use selectable markers on the vectors, for example the tryptophan gene (trp-1) and the lactase gene (lac-4) which originate from *S. cerevisiae* and *K. lactis,* respectively. These DNA-sequences are effective not only as selective markers, but also in enabling a selective pressure to be exerted on the system during further propagation.

Preferably the transcription terminator, if used, is selected from the group consisting of a terminator sequence originating from the Hind III-Eco RI fragment of the 2 micron DNA vector of *S. cerevisiae* and a terminator sequence derived from the GAPDH genes of *S. cerevisiae.*

The presence of a centromer or replicating region derived from a yeast chromosome, e.g. from *S. cerevisiae* or from *K. lactis* improves the stability of the plasmids according to the invention.

The invention further provides a process for preparing a yeast of the genus Kluyveromyces as described above, which process comprises the preparation of a recombinant DNA plasmid by combining a structural gene as indicated above with a KARS-sequence and upstream of the structural gene with a yeast GAPDH regulon and with a selection marker, and optionally with a centromer or replicating region derived from a yeast chromosome and optionally downstream of the structural gene with a transcription terminator derived from a yeast, followed by introducing the plasmid so prepared into a yeast of the Kluyveromyces genus.

Finally the invention provides a process for the microbiological preparation of preprothaumatin or its various allelic or modified forms or their maturation forms disclosed in the above-mentioned European patent applications as well as the proteins so prepared, which process comprises cultivating a yeast of the Kluyveromyces genus as described above, followed by harvesting the thaumatin or thaumatin-like protein thus produced by the yeast.

The invention will be illustrated below in more detail.

Yeasts of the genus Kluyveromyces were chosen, because these micro-organisms comprise many harmless micro-organisms which can be used in foods and drugs manufacture. For example, the species *Kluyveromyces lactis* and *Kluyveromyces fragilis* are safe organisms which are mentioned in the GRAS-list of the Food and Drugs Administration of the USA (GRAS=Generally Recognized As Safe). The behaviour of *K. lactis* in fermentation processes is known to be better than that of *E. coli* and quite controllable; the separation of yeasts from the fermentation fluid is preferable to that of e.g. *E. coli* and often yeasts produce larger quantities of (extra-cellular or periplasmic) proteins than *E. coli.* Therefore yeasts of the genus Kluyveromyces lend themselves better to industrial production than *E. coli.*

Up to now vectors for Kluyveromyces were not known at all.

As a result of extensive research and experimentation new vectors were found which are capable of transforming the host organism *Kluyveromyces lactis* and which, moreover, are able to replicate autonomously in the transformed cell.

The new *K. lactis* vectors control the function of replication and maintenance in *K. lactis.* These replication sequences are the autonomously replicating sequences originating from *Kluyveromyces lactis* (KARS).

Vectors of the KARS type are used because of their high transformation frequency.

The most suitable representative is pKARS-2, a hybrid plasmid composed of a *K. lactis* DNA fragment containing the KARS-2 sequence which is inserted into the known *S. cerevisiae* plasmid YRp7 (Struhl et al., Proc. Natl. Acad. Sci, USA, 76, 1035–1039).

On the vectors there are suitable restriction sites which allow further gene cloning.

Also *Escherichia coli* is a suitable host. In that case the ampicillin resistance gene ($Amp^R$) is also a suitable selectable marker on the vector. The plasmids are preferably multiplied and stored within *E. coli* cells. The transformed strains are selectively grown on L-broth containing ampicillin (100 micrograms/ml). One transformed strain, viz *E. coli* JA 221 (pKARS 12) was deposited with the Central Bureau voor Schimmelcultures, Oosterstraat 1, 3742 SK Baarn, the Netherlands, under number CBS 353.82 (=LMD 82.20) on May 19, 1982. The plasmids can be isolated from the cells by e.g. the method of Katz, L. et al, J. Bacterol. 114 (1973) 577.

The protoplasts of the yeast host are transformed by the aforementioned vectors in a usual incubation medium containing Tris, calcium chloride and polyethylene glycol having a molecular weight ranging from 2,000 to 6,000, but preferably of 4,000.

In using KARS-type plasmids one has the possibility of selecting for the presence of tryptophan prototrophy in the transformants.

The autonomous existence of the KARS-containing plasmids in transformed cells was demonstrated with the aid of DNA analysis. Undigested minilysates of transformants were analyzed according to the Southern procedure, by hybridization with labelled pBR322, the bacterial part of the pKARS plasmids.

Comparative electrophoresis of a minilysate of an untransformed *Kluyveromyces lactis* lac-4 mutant and of purified plasmid preparations shows that only in the transformants hybridizing bands are present with electrophoretic mobilities corresponding to supercoiled and open circular forms of the plasmid used for transformation.

Presence of the plasmid in transformed cells was further confirmed by transforming *E. coli* with the DNA preparation from the yeast transformants and isolating the same plasmids from the *E. coli* transformants formed.

Particularly useful hosts are the mutants *Kluyveromyces lactis* SD11 lac-4 trp-1 and SD69 lac-4, which are derived from the wild type CBS 2360 and deposited with Centraal Bureau voor Schimmelcultures, Oosterstraat 1, 3742 SK Baarn, Netherlands, under numbers SBS 8092 and nr CBS 8093, respectively, on May 19, 1982.

Usually, transforming plasmids remain within the host cell as separate entities capable of autonomous replication and expression. It is pointed out here, however, that genes, located on plasmids (with or without replication sequences) can subsequently also be integrated in the chromosomal DNA of the cell.

The invention is exemplified by a detailed description for the production of preprothaumatin. But the invented process is also applicable for the cloning and expression of other genes encoding for thaumatin-like proteins.

When the invented strains are further adapted for large scale production, it is desirable to remove all bacterial DNA sequences from the vector plasmids.

Genes can remain on autonomously replicating plasmids after having been introduced into the cell or may be integrated in the chromosomal DNA of the host cell.

Isolation of KARS-sequences, their incorporation in recombinant DNA plasmids, and their introduction into cells of *K. lactis*

A. Preparation of recombinant pKARS plasmids 5 micrograms of plasmid YRp7 (Struhl et al., Proc. Natl. Acad. Sci., USA 76, 1035–39 (1979) were digested with restriction-enzyme Sal I. 14 micrograms of DNA from the wild strain *K. lactis* CBS 2360 were digested with enzyme Xho I. The fragments of the plasmid and the *K. lactis* DNA were mixed in a molar ratio of 1:3, forming a DNA fragments mixture.

After inactivation of the restriction-enzymes the solution was brought to a DNA concentration of 25 microorganisms/ml and incubated with T4-ligase under standard conditions (Boehringer).

Transformation of *E. coli* DG75 with the ligated mixture under usual conditions yielded a mixture of $4.5 \times 10^5$ $Amp^R$ transformants, $9 \times 10^3$ of which contained *K. lactis* inserts, as could be deduced from their sensitivity to tetracycline.

The proportion of tetracycline-sensitive cells could be increased to 85% by cycloserine treatment (Bolivar F. and Backman K. (Methods in Enzymology, 68 (1979) 245–267). According to the method of Katz et al. (see Ex. 1) 14 different plasmids were isolated, which were referred to as pKARS 1–14. All were capable of transforming the *K. lactis* SD11 lac-4 trp-1 strain to Trp + phenotype with a frequency of $10^3$–$10^4$ per microgram of DNA. Plasmid pKARS-12 showed the highest transformation frequency of $3 \times 10^4$ per microgram of DNA, but plasmid pKARS-2 appeared to be more convenient in further processing.

The recombinant plasmids obtained could also be transferred to *E. coli* JA221 (trp E5, leu B6, lac y, rec A, hsdM+, hsdR−).

B. *Kluyveromyces lactis* SD11 lac-4 trp-1 transformed to Trp+ with plasmid pKARS-12

Cells of the strain *K. lactis* SD11 lac4 trp-1 were suspended in a growth medium (pH 6.8) containing 1% of yeast extract, 2% of peptone and 2% of glucose. The growth was continued until the exponential phase ($3$–$5.10^7$ cells per ml) had been reached.

The yeast cells were collected by centrifugation, washed with water and resuspended in a solution (pH 8.0) containing 1.2 mol/l sorbitol, 25mmol/l EDTA and 0.2 mol/l fresh mercaptoethanol.

After incubation for 10 min. at 30° C. the cells were centrifuged, washed two times with an 1.2 mol/l sorsorbitol solution and suspended in 20 ml of a solution (pH 5.8) containing 1.2 mol/l sorbitol, 10 mmol/l EDTA, 0.1 mol/l sodium citrate and 10 mg helicase.

Protoplasts were formed and after 15–20 min. there were centrifuged, washed three times with 1.2 mol/l sorbitol and resuspended to a concentration of about $5.10^{10}$ cells per ml in 0.1 ml of a solution containing 10 mmol/l $CaCl_2$ and 1.2 mol/l sorbitol.

10 micrograms of pKARS-12 DNA were added and the mixture was incubated for 15 min. at 25° C. Thereafter 0.5 ml of a solution (pH 7.5) containing 10 mmol/l Tris, 10 mmol/l $CaCl_2$ and 20% (w/v) polyethylene glycol 4000 was added, followed by 20 min. incubation.

Protoplasts were precipitated by centrifugation and then resuspended to a concentration of about $5.10^{10}$ protoplasts per ml in a solution (pH 6.8) containing 7 mmol/l $CaCl_2$, 1.2 mol/l sorbitol, 0.5 mg/ml yeast extract, 1 mg/ml peptone and 2 mg/ml glucose.

After incubation for 60 min. at 30° C. the protoplasts were centrifuged, washed with 0.6 mol/1 KCl solution and resuspended in 0.6 mol/1 KCl solution.

In order to be able to select the Trp+ transformants, $1.10^9$ protoplasts were brought on 2% agar minimal plates (with 3% agar overlay) containing 2% of glucose and 0.6 mol/1 KCl.

Colonies appeared within 4-5 days. On 0.6 mol/1 KCl plates with glucose as carbon source protoplast regeneration is usually 0.5-1.5%. Per microgram of pKARS12 DNA $3.4 \times 10^4$ Trp+ transformants were obtained.

DNA preparations were made according to Struhl et al. (Proc. Natl. Acad. Sci., USA 76, 1035-1039, (1979).

C. *Kluyveromyces lactis* SD69 lac-4 transformed to Trp+ with KARS-type plasmids Analogously to the method described in B transformation experiments could be carried out with other KARS-type plasmids. The results of the experiments are summarized in the following Table.

TABLE

| Strain | Genotype | Plasmid | Transformants per microgram DNA | Size of KARS fragments |
|---|---|---|---|---|
| SD11 | lac-4 trp-1 | pKARS1 | $1.5 \times 10^3$ | 2.24 |
| SD11 | lac-4 trp-1 | pKARS2 | $5 \times 10^3$ | 1.24 |
| SD11 | lac-4 trp-1 | pKARS7 | $10^3$ | 2.3 |
| SD11 | lac-4 trp-1 | pKARS8 | $5 \times 10^3$ | 1.85 |
| SD11 | lac-4 trp-1 | pKARS10 | $2.4 \times 10^4$ | 3.15 |
| SD11 | lac-4 trp-1 | pKARS12 | $3.4 \times 10^4$ | 5.0 |
| SD11 | lac-4 trp-1 | pKARS13 | $1.5 \times 10^4$ | 2.0 |
| SD11 | lac-4 trp-1 | pKARS14 | $1.8 \times 10^4$ | 2.15 |

The molecular weights of pKARS plasmids were determined after digestion with Eco RI and Hind III endonucleases, using 0.8% of agarose gel and the usual molecular weight markers.

The following detailed description will illustrate the isolation of the GAPDH regulon and its introduction into preprothaumatin encoding plasmids.

D. Isolation of clones containing the glyceraldehyde-3-phosphate dehydrogenase (GAPDH) operon of *S. cerevisiae*.

Unless stated otherwise, all enzyme incubations were carried out under conditions described by the supplier. Enzymes were obtained from Amersham, Boehringer, BRL or Biolabs.

A DNA pool of the yeast *S. cerevisiae* was prepared in the hybrid E. coli-yeast plasmid pFl1 (M. R. Chevallier et al. Gene 11, 11-19 (1980)) by a method similar to the one described by M. Carlson and D. Botstein, Cell 28, 145-154 (1982). Purified yeast DNA was partially digested digested with restriction endonuclease Sau 3A and the resulting DNA fragments (with an average length of 5 kb) were ligated by T4 DNA ligase in the dephosphorylated Bam HI site of PFl1. After transformation of CaCl$_2$-treated *E. coli* cells with the ligated material a pool of about 30.000 ampicillin resistant clones was obtained. These clones were screened by a colony hybridization procedure (R. E. Thayer, Anal. Biochem., 98, 60-63 (1979)) with a chemically synthesized and $^{32}$p-labelled oligomer with the sequence 5'TACCAGGAGACCAACTT3'.

Figure 1:
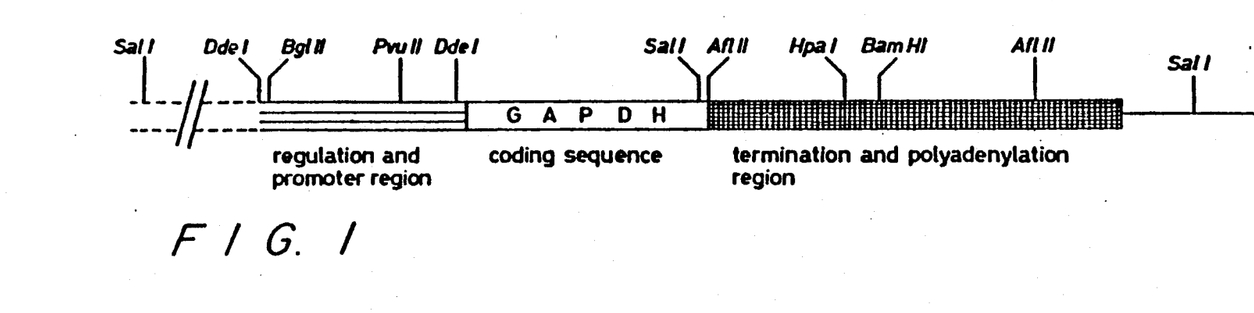
Figure 2:
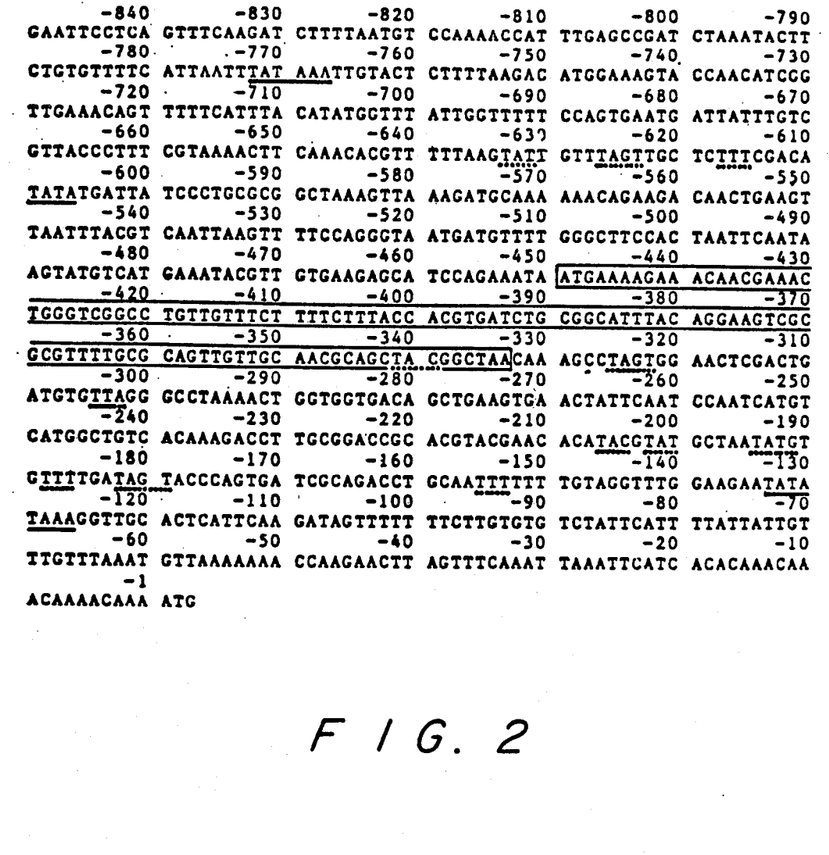

According to data published by J. P. Holland and M. J. Holland (J. Biol. Chem., 255, 2596-2605, 1980) this oligomer is complementary with the DNA sequence encoding aminoacids 306-310 (the wobble base of the last amino acid was omitted from the oligomer) of the GAPDH gene. Using hybridization conditions described by R. B. Wallace et al., Nucleic Acid Res., 9, 879-894(1981), six positive transformants could be identified. One of these harboured plasmid PFl1-33. The latter plasmid contained the GAPDH gene including its promoter/regulation region and its transcription termination/polyadenylation region. The approximately 9 kb long insert of pFl 1-33 has been characterized by restriction enzyme analysis (FIG. 1) and partial nucleotide sequence analysis (FIGS. 2 and 3).

E. Isolation of the GAPDH promoter/regulation region and its introduction into a preprothaumatin encoding plasmid (FIG. 4)

On the basis of the restriction enzyme analysis and the nucleotide sequence data of the insert of plasmid pFl 1-33, the RNA initiation/regulation region of the GAPDH gene was isolated as an 800 nucleotides long Dde I fragment. To identify this promoter fragment, plasmid pFl 1-33 was digested with Sal I and the three resulting DNA fragments were subjected to a Southern hybridization test with the chemically synthesized oligomer [E. M. Southern, J. Mol. Biol. 98, 503-517 (1975)]. A positively hybridizing 4.3 kb long restriction fragment was isolated on a preparative scale by electroelution from a 0.7% agarose gel and was then cleaved with Dde I. Of the resulting Dde I fragments only the largest one had a recognition site for Pvu II, a cleavage site located withion the GAPDH regulon region (FIG. 1). The largest Dde I fragment was isolated and incubated with Klenow DNA polymerase and four dNTP's (A. R. Davis et al., Gene 10, 205-218 (1980)) to generate a blunt-ended DNA molecule. After extraction of the reaction mixture with phenol/chloroform (50/50 v/v), passage of the aquous layer through a Sephadex G50 column and ethanol precipitation of the material present in the void volume, the DNA fragment was equipped with the $^{32}$p-labelled Eco RI linker 5'GGAATTCC3' by incubation with T4 DNA ligase. Owing to the Klenow DNA polymerase reaction and the subsequent ligation of the Eco RI linker, the original Dde I sites were reconstructed at the ends of the regulon fragment. To inactivate the ligase the reaction mixture was heated to 65° C. for 10 minutes, then sodium chloride was added (final concentration 50 mmol/1) and the whole mix was incubated with Eco RI. Incubation was terminated by extraction with phenol/chloroform, the DNA was precipitated twice with ethanol, resuspended and then ligated into a suitable vector molecule. Since the Dde I regulon fragment was equipped with Eco RI sites, it can easily be introduced into the Eco RI site of pUR 528 (EP-PA 54331) to create a plasmid in which the yeast regulon is adjacent to the structural gene encoding preprothaumatin. The latter plasmid was obtained by cleavage of pUR 528 with Eco RI, treatment of the linearized plasmid molecule with (calf intestinal) alkaline phosphatase to prevent self-ligation and incubation of each of these vector molecules, as well as the purified Dde I promoter fragment, with T4 DNA ligase. Transformation of the various ligation mixes in CaCl$_2$-treated *E. coli* HB101 cells yielded several ampicillin resistant colonies. From some of these colonies plasmid DNA was isolated (H. C. Birnboim and J. Doly, Nucleic Acids Res. 7, 1513-1523 (1979)), and incubated with PvuII to test the orientation of the insert.

Figure 4:
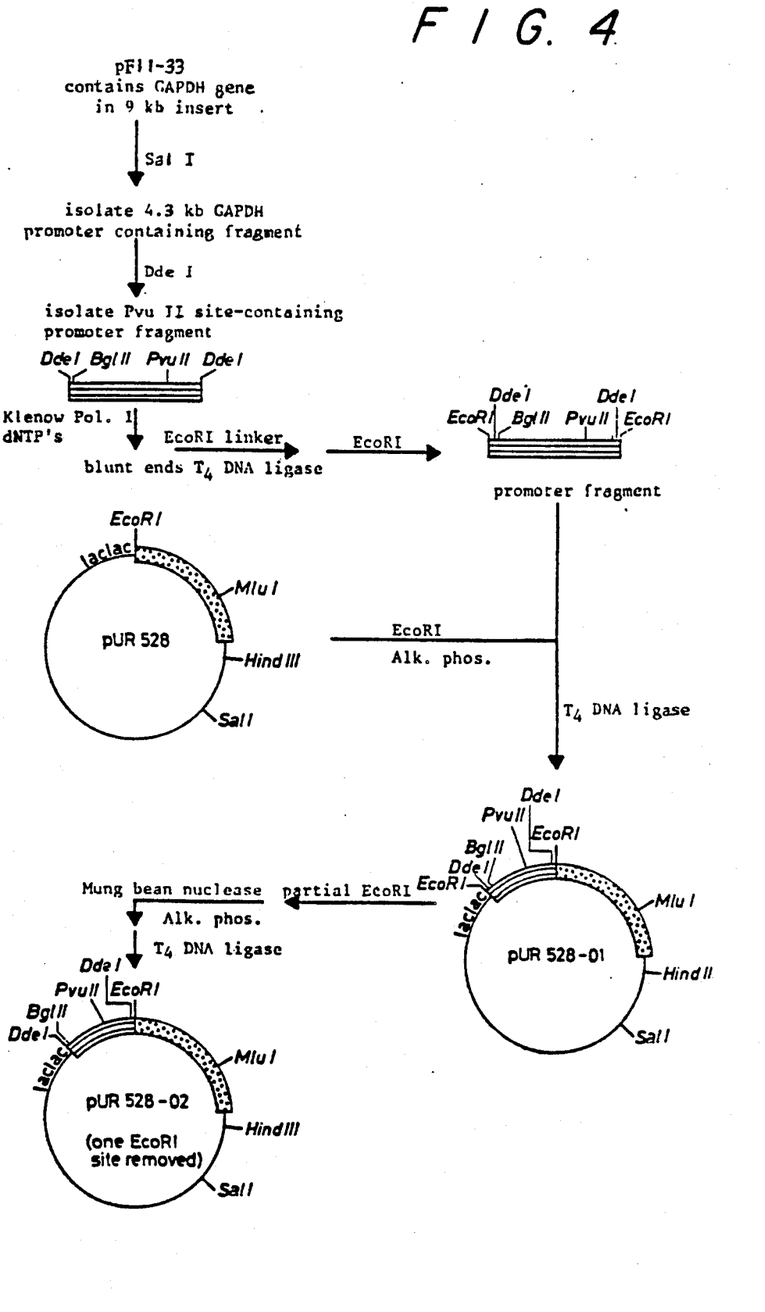

In the nomenclature plasmids containing the Eco RI (Dde I) GAPDH regulon fragment in the correct orientation (i.e. transcription from the GAPDH regulon occurs in the direction of a downstream located structural gene) are indicated by the addendum-01 to the original code of the plasmid (for example pUR 528 is changed in pUR 528-01; see FIG. 4).

To facilitate manipulation of plasmids containing the Eco RI regulon fragment, one of the two Eco RI sites was destroyed. Two µg of plasmid DNA (e.g. pUR 528-01) was partially digested with Eco RI and then incubated with 5 units Mung bean nuclease (obtained from P. L. Biochemicals Inc.) in a total volume of 200 µl in the presence of 0.05 moles/l sodium acetate (pH 5.0), 0.05 moles/l sodium chloride and 0.001 moles/l zinc chloride for 30 minutes at room temperature to remove sticky ends. The nuclease was inactivated by addition of SDS to a final concentration of 0.1% (D. Kowalski et al., Biochemistry 15, 4457–4463 (1976) and the DNA was precipitated by the addition of 2 volumes of ethanol (in this case the addition of 0.1 volume of 3 moles/l sodium acetate was omitted). Linearized DNA molecules were then religated by incubation with T4 DNA ligase and used to transform CaCl$_2$-treated E. coli cells. Plasmid DNA isolated from ampicillin resistant colonies was tested by cleavage with Eco RI and Mlu I for the presence of a single Eco RI site adjacent to the preprothaumatin gene (cf. FIG. 4).

Plasmids containing the GAPDH promoter fragment but having only a single Eco RI recognition site adjacent to the ATG initiation codon of a downstream located structural gene, are referred to as -02 type plasmids (for example: pUR 528-01 is changed in pUR 528-02; see FIG. 4).

F. Reconstitution of the original GAPDH promoter/regulation region in plasmids encoding preprothaumatin by introduction of a synthetic DNA fragment (FIG. 5, 6)

Figure 7:
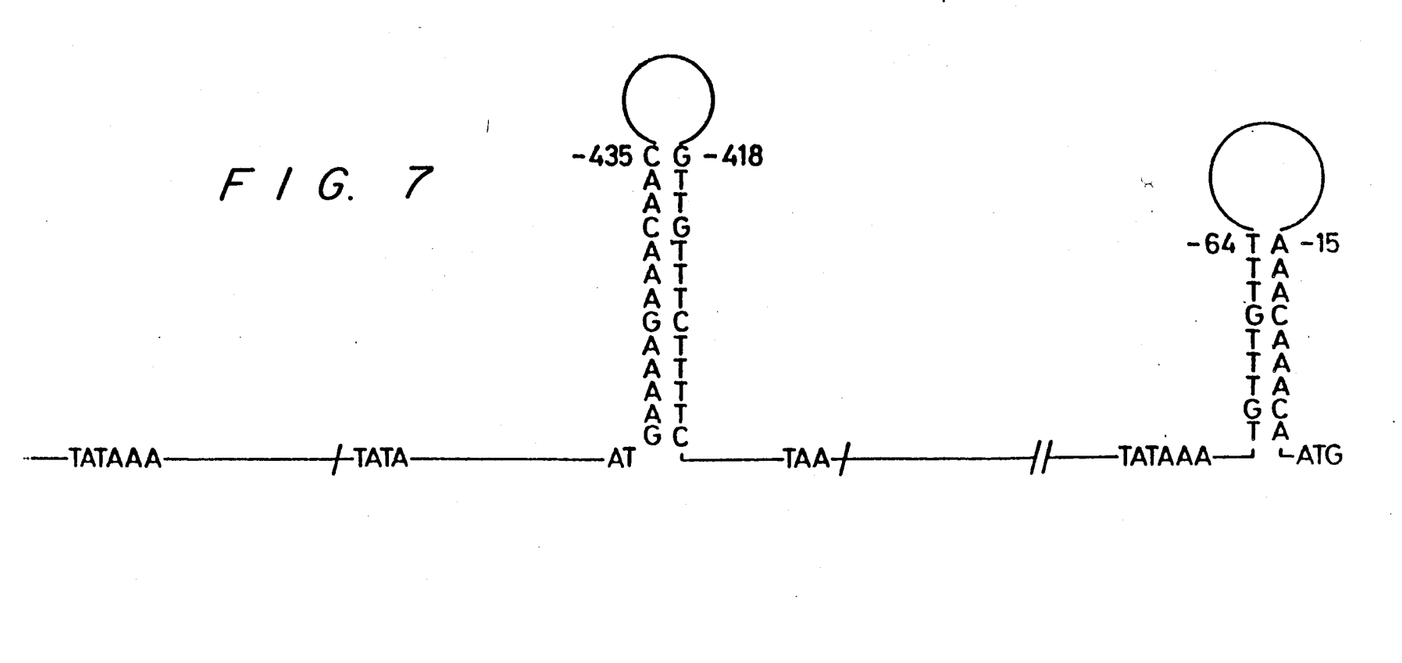

As shown by the nucleotide sequence depicted in FIG. 2, THE Eco RI Dde I) GAPDH promoter fragment contains the nucleotides -850 to -39 of the original GAPDH promoter/regulation region. Not contained in this promoter fragment are the 38 nucleotides preceding the ATG initiation codon of the GAPDH encoding gene. The latter 38-nucleotides long fragment contains the PuCACACA sequence, which is found in several yeast genes. Said PuCACACA sequence, situated about 20 bp upstream of the translation start site (M. J. Dobson et al., Nucleic Acid Res., 10, 2625-2637 (1982)), provides the nucleotide sequence upstream of the ATG codon which is optimal for protein initiation. (M. Kozak, Nucleic Acids Res. 9, 5233-5252 (1981)). Moreover, as shown in FIG. 7, these 38 nucleotides allow the formation of a loop structure which might be involved in the regulation of expression of the GAPDH gene. On the basis of the above-mentioned arguments, introduction of the 38 nucleotides between the Dde I promoter-fragment and the ATG codon of a downstream located structural gene was considered necessary to improve promoter activity as well as translation initiation.

Figure 5:
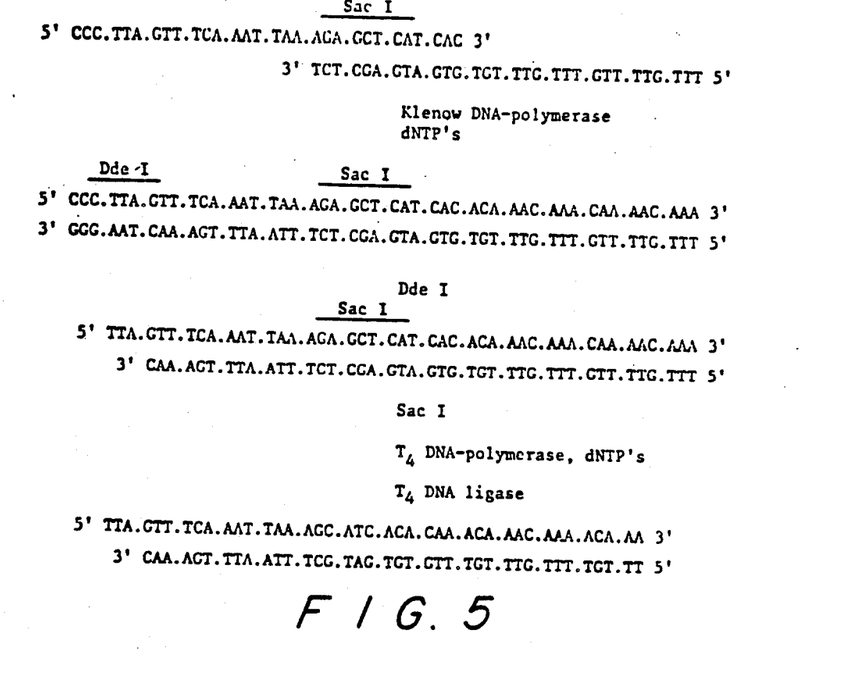

As outlined in FIG. 5 the missing DNA fragment was obtained by the chemical synthesis of two partially overlapping oligomers. The Sac I site present in the overlapping part of the two oligonucleotides was introduced for two reasons: (i) to enable manipulation of the nucleotide sequence immediately upstream of the ATG codon including the construction of poly A-tailed yeast expression vectors. (ii) to give a cleavage site for an enzyme generating 3'-protruding ends that can easily and reproducibly be removed by incubation with T4 DNA polymerase in the presence of the four dNTP's. Equimolar amounts of the two purified oligomers were phosphorylated at their 5'-termini, hybridized (J. J. Rossi et al., 1982, J. Biol. Chem. 257, 9226-9229) and converted into a double-stranded DNA molecule by incubation with Klenow DNA polymerase and the four dNTP's under conditions which have been described for double-stranded DNA synthesis (A. R. Davis et al., Gene 10, 205-218 (1980)). Analysis of the reaction products by electrophoresis through a 13% acrylamide gel followed by autoradiography showed that more than 80% of the starting single-stranded oligonucleotides were converted into double-stranded material. The DNA was isolated by passage of the reaction mix over a Sephadex G50 column and ethanol precipitation of the material present in the void volume. The DNA was then phosphorylated by incubation with polynucleotide kinase and digested with Dde I. To remove the nucleotides cleaved off in the latter reaction, the reacton mix was subjected to two precipitations with ethanol.

Figure 6:
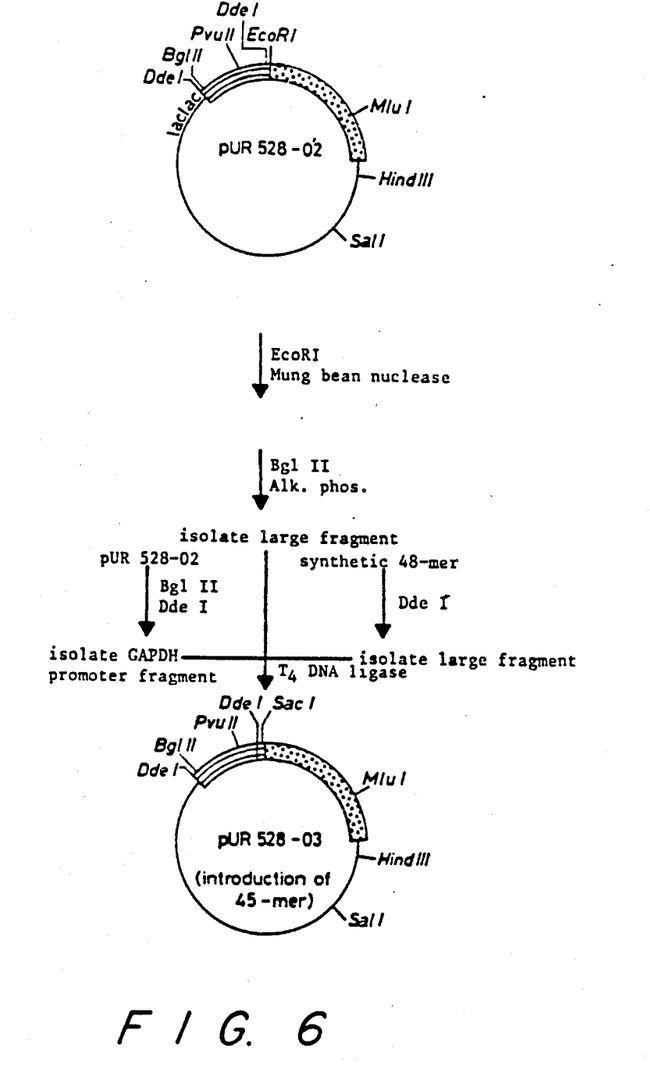

As shown in FIG. 6 cloning of the resulting synthetic DNA fragment was carried out by the simultaneous ligation of this fragment and a Bgl II-DdE I GAPDH promoter regulation fragment in a vector molecule from which the Eco RI site preceding the ATG initiation codon was removed by Mung bean nuclease digestion (cf. E.). The Bgl II-Dde I promoter/regulation fragment was obtained by digestion of plasmid pUR 528-02 with Dde I and Bgl II. Separation of the resulting restriction fragments by electrophoresis through a 2agerose gel and subsequent isolation of the fragment from the gel yielded the purified 793 nucleotides long promoter/regulation fragment. In the plasmid pUR 528-02 the nucleotide sequence preceding the ATG codon is 5'-GAATTC(T)ATG-3' (EP-PA 54330 and EP-PA 54331), which is different from the favourable nucleotide sequence given by M. Kozak (Nucleic Acids Res. 9, 5233–5252 (1981)). Since our aim was to reconstitute the original GAPDH promoter/regulation/-protein initiation region as accurately as possible, the Eco RI site was removed in order to ligate the synthetic DNA fragment to the resulting blunt-end. Removal of the Eco RI site was accomplished by Mung bean nuclease digestion of Eco RI-cleaved pUR528-02 DNA (see E.).

Subsequently the plasmid DNA was digested with Bgl II and incubated with phosphatase. After separation of the two DNA fragments by electrophoresis through a 0.7% agarose gel, the largest fragment was isolated and used as the vector in which the Bgl II-Dde I promoter fragment as well as the - Dde I-treated- synthetic DNA fragment were ligated.

Plasmids in which the Dde I promoter/regulation fragment together with the Sac I recognition site containing synthetic DNA fragment are introduced are indicated by the addendum -03 (for example: pUR 528-02 is changed into pUR 528-03).

Figure 8:
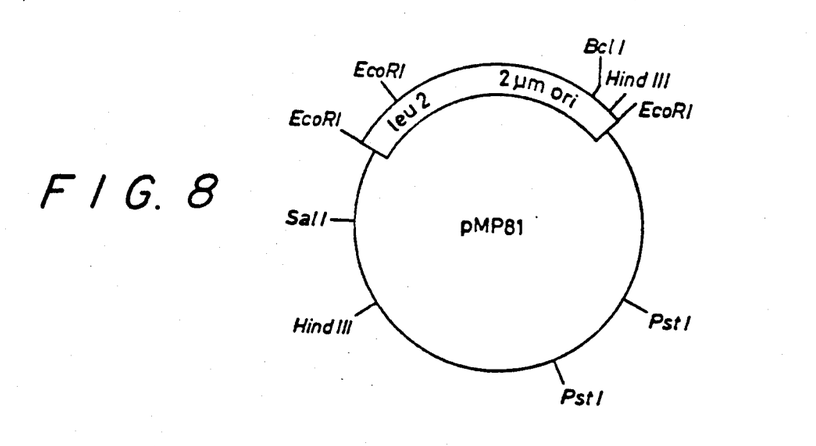
Figure 9:
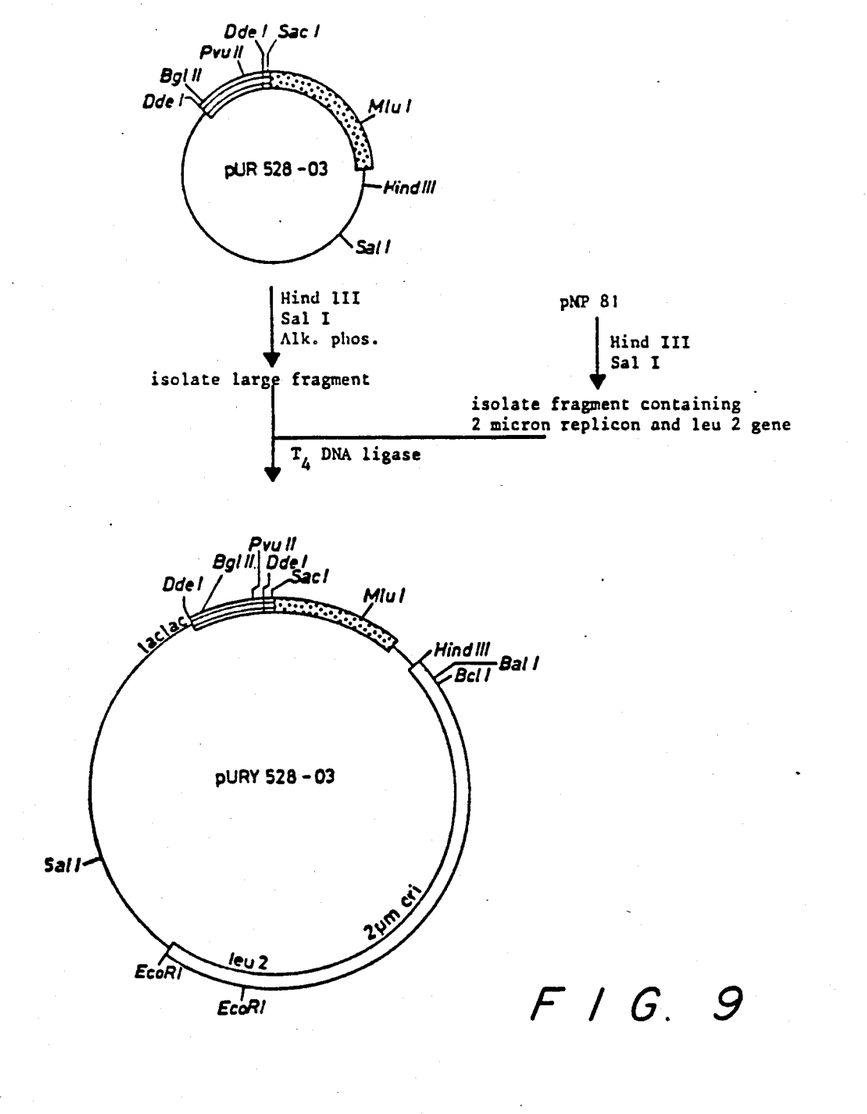

G. Introduction of 2 µm DNA replication origin and the yeast leu-2 gene in preprothautmatin encoding plasmids To test the functionality of the GAPDH regulon in S. cerevisiae, plasmids pUR528-02 and pUR528-03 equipped with a replication origin obtained from the yeast 2 µm DNA and a selectable marker. Both functions were excised from plasmid pMP81 and introduced into the two preprothaumatin encoding plasmids. The E. coli-yeast shuttle vector pM81 (FIG. 8; C. P. Hollenberg, Current Topics in Microbiol. and Immun., 96, 119-144, (1982)) consists of plasmid pCRI (C. Covey et al., MGG, 145, 155-158 (1976)) and a double Eco RI fragment of pJDB 219 (J. D. Beggs, Nature, 275, 104-109 (1978)) carrying both the leu-2 gene and the yeast 2 μm DNA replication origin. The last mentioned two functions were excised from pMP81 by a digestion with Hind III and Sal I. The resulting 4.4 kb long restriction fragment was combined with pUR 528-02 or pUR 528-03 derivatives containing preprothaumatin gene and with a GAPDH promoter/regulation region of S. cerevisiae to form plasmids. This was accomplished by cleavage of said plasmids with Hind III and Sal I (cf. FIG. 6, 9) and a subsequent treatment of the resulting fragments with phosphatase. After separation of the fragments by electrophoresis through a 1% agarose gel, the largest fragment was isolated, mixed with the purified Hind III-Sal I fragment obtained from pMP81, ligated with T4 DNA ligase and transformed to CaCl$_2$-treated E. coli cells. From some of the ampicillin-resistant transformants plasmid DNA was isolated and subjected to restriction enzyme analysis. Plasmids containing the correct insert (pURY 528-02 or pURY 528-03) were purified by CsCl-ethidium bromide density gradient centrifugation and used to transform S. cerevisiae (A. Hinnen et al., Proc. Natl. Acad. Sci. USA 75, 1929-1033 (1978)) according to the procedure of J. D. Beggs, Nature 275, 104-109 (1978).

H. Introduction of KARS-2 and the trp-1 gene in preprothaumatin encoding plasmids The E. coli yeast shuttle vector pEK 2-7 consists of plasmid YRp7 (D. T. Stinchbomb et al., Nature 282, 39-43 (1979)) containing the 1,2 kb KARS-2 fragment. Owing to the presence of the yeast trp-1 gene, plasmid pEK 2-7 can be maintained in K. lactis SD11 lac-4, trp-1; (the preparation of pEK 2-7 is described in European/PCT application No. 83/00128, published WO/83/04050, claiming priority of Netherlands patent application No. 8202091).

Figure 10:
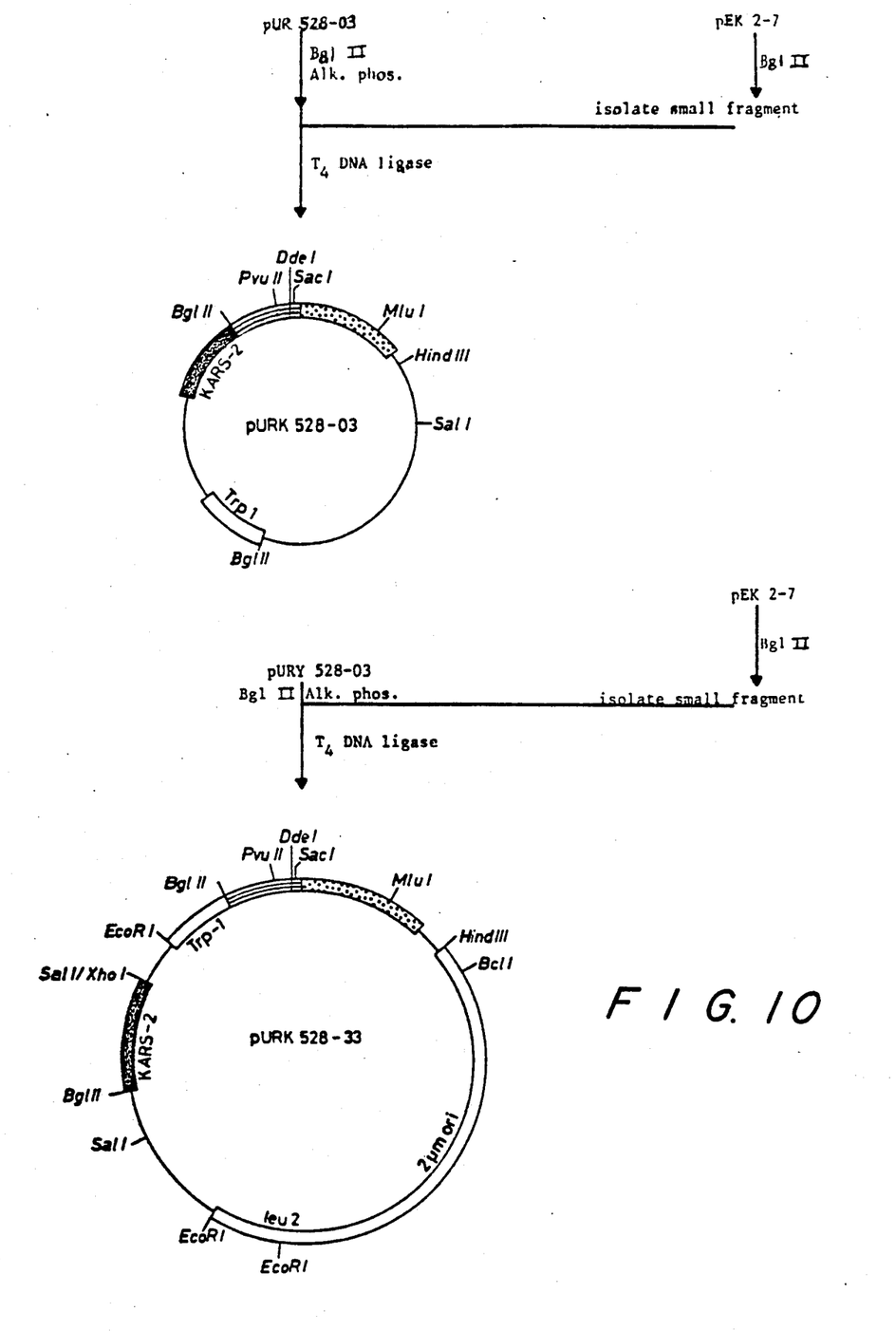
Figure 11:
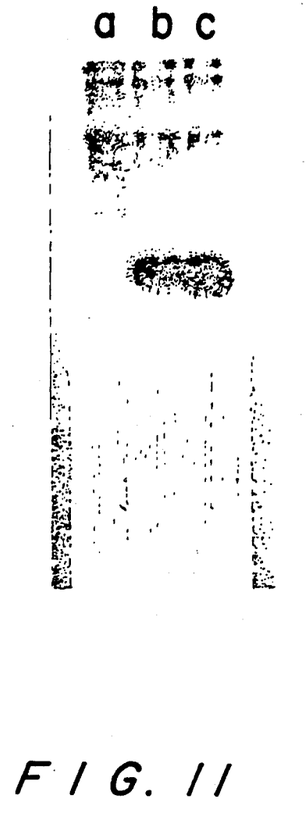

To demonstrate the functionality of the promoter/regulation region of the GAPDH encoding gene in K. lactis, plasmid pUR 528-03 (FIG. 9) has been equipped with both the KARS-2 fragment and the trp-1 gene. The last-mentioned two functions were excised from pEK 2-7 by a digestion with Bgl II, followed by isolation from a 0.7% agarose gel of the smallest fragment generated. This purified fragment was then inserted in the dephosphorylated Bgl II cleavage site of pUR 528-03 by incubation with T4 DNA ligase. Transformation of the ligation mix in CaCl$_2$-treated E. coli cells yielded plasmid pURK 528-03 (FIG. 10). Transformants generated by the introduction of the latter plasmid into K. lactis SD 11 cells by the procedure described in Netherlands patent application No. 8202091 could be shown to synthesize thaumatin-like protein (FIG. 11).

By techniques similar to those mentioned above, plasmid pURY 528-03 (see G) was also equipped with the KARS-2 fragment and the yeast trp-1 gene and introduced into K. lactis SD 11 (FIG. 10).

I. Expression in K. lactis of the preprothaumatin encoding genes under control of the promoter/regulation region of the glyceraldehyde-3-phosphate dehydrogenase operon of S. cerevisiae Using the same detection procedure, K. lactis cells carrying pURK 528-33 could also be shown to synthesize a thaumatin-like protein (FIG. 11). The production of thaumatin-like proteins in cells containing pURK 528-33 was, however, about 3 times higher than in cells containing pURK 528-03. Since similar observations have been made by C. Gerbaud et al. Gene 5, 233-253 (1979) in the expression of the yeast ura-3 gene upon insertion of this gene within the coding region "Able" of the 2 μm DNA, it is very likely that the enhanced expression of thaumatin-like protein by pURK 528-33 is due to efficient transcription termination events in the transcription/polyadenylation of the "Able" operon. This observation indicates that the presence of an efficient transcription termination/polydenylation region downstream of a an efficient transcription of a structural gene transcribed by the GAPDH promoter/regulation region is an important factor in optimizing gene expression. It is to be expected that substitution of the "Able-terminator" by the GAPDH termination polyadenylation region (FIG. 3) will give at least a similar improvement in the expression.

We claim:
1. Yeast of the genus Kluyveromyces containing a recombinant DNA plasmid comprising
   (i) a structural gene coding for a thaumatin-like product selected from the group consisting of
      (a) preprothaumatin,
      (b) prethaumatin,
      (c) prothaumatin, and
      (d) thaumatin,
   (ii) an autonomously replicating sequence from Kluyveromyces lactis CBS2360 (so-called KARS), and
   (iii) a yeast regulon from the glyceraldehyde-3-phosphate dehydrogenase (GAPDH) genes of Saccharomyces cerevisiae,
said yeast being capable of expressing the thaumatin-like product coded for in the recombinant DNA plasmid.

2. Yeast according to claim 1, said yeast being a Kluyveromyces lactis yeast.

3. Yeast according to claim 1, wherein said recombinant DNA plasmid therein comprises a KARS-sequence from the wild strain K. lactis CBS2360.

4. Yeast according to claim 1, wherein said recombinant DNA plasmid therein further comprises at least one member of the group consisting of a selection marker, a yeast transcription terminator, a yeast centromer and a yeast replication region.

5. A process for preparing a yeast of the genus Kluyveromyces according to claim 1, comprising the steps of preparing a recombinant DNA plasmid comprising
   (i) a structural gene coding for a thaumatin-like product selected from the group consisting of
      (a) preprothaumatin,
      (b) prethaumatin,
      (c) prothaumatin, and
   (ii) an autonomously replicating sequence from Kluyveromyces lactis CBS 2360 (so-called KARS), and (iii) a yeast regulon from the glyceraldehyde-3-phosphate dehydrogenase (GAPDH) genes of *Saccharomyces cerevisiae*,
and introducing said plasmid into a yeast of the genus Kluyveromyces, the yeast so prepared being capable of expressing the thaumatin-like product coded for in the recombinant DNA plasmid.

6. A process according to claim 5, said yeast being a *Kluyveromyces lactis* yeast.

7. A process according to claim 5, wherein said recombinant DNA plasmid therein comprises a KARS-sequence from the wild strain *K. lactis* CBS2360.

8. A process according to claim 5, wherein said recombinant DNA plasmid therein further comprises at least one member selected from the group consisting of a selection marker, a yeast transcription terminator, a yeast centromer and a yeast replication region.

9. A process for microbiologically preparing a thaumatin-like product selected from the group consisting of
    (a) preprothaumatin,
    (b) prethaumatin,
    (c) prothaumatin, and
wherein a yeast of the genus Kluyveromyces as claimed in claim 1 is cultivated and the thaumatin-like product produced by the yeast is harvested.

* * * * *

UNITED STATES PATENT AND TRADEMARK OFFICE
CERTIFICATE OF CORRECTION

PATENT NO. : 4,657,857

DATED : April 14, 1987

INVENTOR(S) : EDENS, L; LEDEBOER, A; VERRIPS, C; VAN DEN BERG, J.

It is certified that error appears in the above-identified patent and that said Letters Patent is hereby corrected as shown below:

Claim 5, between lines 9 and 10 (Column 10, between lines 65 and 66 of patent), insert -- (d) thaumatin, --.

Claim 9, between lines 6 and 7 (Column 12, between lines 9 and 10 of patent), insert -- (d) thaumatin, --.

Signed and Sealed this

Fifth Day of April, 1988

Attest:

DONALD J. QUIGG

Attesting Officer

Commissioner of Patents and Trademarks